United States Patent
Drontle et al.

(10) Patent No.: US 11,406,406 B2
(45) Date of Patent: Aug. 9, 2022

(54) TURBINATE COMPRESSORS AND METHODS OF USE

(71) Applicant: Entellus Medical, Inc., Maple Grove, MN (US)

(72) Inventors: John R. Drontle, Buffalo, MN (US); Anthony J. Hanson, Chaska, MN (US)

(73) Assignee: Entellus Medical, Inc., Maple Grove, MN (US)

(*) Notice: Subject to any disclaimer, the term of this patent is extended or adjusted under 35 U.S.C. 154(b) by 489 days.

(21) Appl. No.: 16/672,436

(22) Filed: Nov. 2, 2019

(65) Prior Publication Data

US 2020/0060705 A1 Feb. 27, 2020

Related U.S. Application Data

(62) Division of application No. 15/205,928, filed on Jul. 8, 2016, now abandoned.

(60) Provisional application No. 62/190,175, filed on Jul. 8, 2015.

(51) Int. Cl.
*A61B 17/24* (2006.01)
*A61B 17/28* (2006.01)

(52) U.S. Cl.
CPC .......... *A61B 17/24* (2013.01); *A61B 17/282* (2013.01)

(58) Field of Classification Search
CPC ....... A61B 17/24; A61B 17/28; A61B 17/282; A61B 17/1739; A61B 2017/2926; A61B 2018/00327; A61B 1/233; A61B 18/1485
See application file for complete search history.

(56) References Cited

U.S. PATENT DOCUMENTS

| | | |
|---|---|---|
| 4,712,545 A | 12/1987 | Honkanen |
| 5,395,369 A | 3/1995 | McBrayer et al. |
| 7,520,876 B2 | 4/2009 | Ressemann et al. |
| 7,678,099 B2 | 3/2010 | Ressemann et al. |
| 7,842,062 B2 | 11/2010 | Keith et al. |
| 7,879,061 B2 | 2/2011 | Keith et al. |
| 7,918,871 B2 | 4/2011 | Truitt et al. |
| 8,241,266 B2 | 8/2012 | Keith et al. |
| 8,277,478 B2 | 10/2012 | Drontle et al. |
| 8,282,667 B2 | 10/2012 | Drontle et al. |
| 8,348,969 B2 | 1/2013 | Keith et al. |
| 8,568,439 B2 | 10/2013 | Keith et al. |
| 8,585,728 B2 | 11/2013 | Keith et al. |
| 8,585,729 B2 | 11/2013 | Keith et al. |
| 8,623,043 B1 | 1/2014 | Keith et al. |
| 8,657,846 B2 | 2/2014 | Keith et al. |
| 8,801,670 B2 | 8/2014 | Drontle et al. |

(Continued)

OTHER PUBLICATIONS

Busaba, Nicolas, In Response to Reformation of Concha Bullosa Following Treatment by Crushing Surgical Technique: Implication for Balloon Sinuplasty, Laryngoscope. 2010;120(7):1492 (Letter).

(Continued)

*Primary Examiner* — Sarah W Aleman
(74) *Attorney, Agent, or Firm* — McDonnell Boehnen Hulbert & Berghoff LLP

(57) ABSTRACT

Surgical forceps suited for use in the compression of turbinates in the human nasal system. The forceps are designs to prevent excessive tissue trauma as the turbinates are compressed. The compressed turbinates can provide additional maneuvering room within the nasal anatomy to perform subsequent surgical procedures.

20 Claims, 10 Drawing Sheets

(56) References Cited

U.S. PATENT DOCUMENTS

| | | |
|---|---|---|
| 8,834,513 B2 | 9/2014 | Hanson et al. |
| 8,882,795 B2 | 11/2014 | Drontle et al. |
| 8,888,686 B2 | 11/2014 | Drontle et al. |
| 8,915,938 B2 | 12/2014 | Keith et al. |
| 9,005,284 B2 | 4/2015 | Ressemann |
| 9,101,739 B2 | 8/2015 | Lesch, Jr. et al. |
| 9,192,748 B2 | 11/2015 | Ressemann et al. |
| 9,278,199 B2 | 3/2016 | Keith et al. |
| 9,282,986 B2 | 3/2016 | Hanson et al. |
| 9,283,360 B2 | 3/2016 | Lesch et al. |
| 9,320,876 B2 | 4/2016 | Ressemann et al. |
| 9,333,327 B2 | 5/2016 | Setliff, III et al. |
| 9,339,637 B2 | 5/2016 | Drontle et al. |
| 9,370,650 B2 | 6/2016 | Hanson et al. |
| 9,433,343 B2 | 9/2016 | Drontle et al. |
| 9,440,049 B2 | 9/2016 | Drontle et al. |
| 9,486,614 B2 | 11/2016 | Drontle et al. |
| 9,550,049 B2 | 1/2017 | Hanson et al. |
| 9,694,167 B2 | 7/2017 | Keith et al. |
| 9,700,705 B2 | 7/2017 | Lesch, Jr. et al. |
| 9,775,975 B2 | 10/2017 | Ressemann et al. |
| 10,022,525 B2 | 7/2018 | Hanson et al. |
| 10,029,069 B2 | 7/2018 | Keith et al. |
| 10,086,181 B2 | 10/2018 | Lesch et al. |
| 2005/0049633 A1 | 3/2005 | Watanabe |
| 2005/0113850 A1* | 5/2005 | Tagge ............... A61B 17/0469 606/139 |
| 2005/0222610 A1* | 10/2005 | Melker ............. A61B 17/0482 606/205 |
| 2008/0172033 A1 | 7/2008 | Keith et al. |
| 2010/0076485 A1* | 3/2010 | Gonzales ........... A61B 17/0401 606/213 |
| 2011/0021975 A1* | 1/2011 | Covello ................ A61M 29/02 606/199 |
| 2016/0151614 A1 | 6/2016 | Ressemann et al. |
| 2016/0166814 A1 | 6/2016 | Lesch et al. |
| 2016/0367286 A1 | 12/2016 | Drontle et al. |
| 2017/0028112 A1 | 2/2017 | Drontle et al. |
| 2017/0050001 A1 | 2/2017 | Drontle et al. |
| 2017/0113027 A1 | 4/2017 | Drontle et al. |
| 2017/0368319 A1 | 12/2017 | Lesch, Jr. et al. |
| 2018/0008806 A1 | 1/2018 | Ressemann et al. |
| 2018/0304051 A1 | 10/2018 | Keith et al. |
| 2018/0304058 A1 | 10/2018 | Hanson et al. |

OTHER PUBLICATIONS

Dogru, Harun et al., Concha bullosa squeezer for turbinoplasty (Dogru forceps). J Otolaryngol. 2004;33:111-113.

Eren, Sabri baki et al., A comparison of the long-term results of crushing and crushing with intrinsic stripping techniques in concha bullosa surgery. Int Forum Allergy Rhinol. 2014;4(9):753-758.

Har-El, Gady et al., Turbinoplasty for concha bullosa: a non-synechia forming alternative to middle turbinectomy. Rhinology. 1996; 34:54-56.

Hasegawa, Makoto et al., Postoperative mucoceles of the maxillary sinus, Rhinology, XVII, 253-256, 1979.

Kieff, David A et al., Reformation of Concha Bullosa Following Treatment by Crushing Surgical Technique: Implication for Balloon Sinuplasty. Laryngoscope. 2009;119(12):2454-2456.

Pentilla, Matti, In reference to reformation of concha bullosa following treatment by crushing surgical technique: Implication for balloon sinuplasty. Laryngoscope. 2010;120(7):1491 (Letter).

Tanyeri, Hasan et al., Will a crushed concha bullosa form again? Laryngoscope. 2012;122(5):956-960.

Unlu, H. Halis et al., Concha Bullosa, The Journal of Otolaryngology, 1994; 23(1): 23-27.

Woolford, T.J. et al., Short Communication, A concha bullosa crusher for use in endoscopic sinus surgery, The Journal of Laryngology and Otology, Mar. 2000, vol. 114, pp. 205-206.

\* cited by examiner

TURBINATE COMPRESSORS AND METHODS OF USE

RELATED APPLICATION

This patent application is a divisional of U.S. patent application Ser. No. 15/205,928, filed on Jul. 8, 2016, which claims the benefit of priority of U.S. Provisional Patent Application Ser. No. 62/190,175, entitled "Turbinate Compressor," filed on Jul. 8, 2015, which are incorporated by reference herein in their entirety.

BACKGROUND

Surgical procedures are commonly performed within the nasal anatomy of humans. Balloon sinuplasty, for example, has become an important method of treating sinusitis in recent years. A balloon is advanced into a drainage pathway of a nasal sinus cavity and inflated. The inflated balloon expands the drainage pathway, thereby providing for improved drainage of the sinus cavity.

It is often challenging to maneuver surgical instruments within the nasal anatomy. The mucosal tissue lining the nasal anatomy is often diseased and inflamed. Further, anatomical structures (e.g., nasal conchae or turbinates) may obstruct access to desired locations within the nasal and sinus systems.

Overview

Balloon sinuplasty procedures, as well as other surgical procedures performed in the nasal or sinus anatomy, can often be complicated by anatomical features. The features may make it difficult or impossible for a surgeon to access a desired anatomical location.

The present inventors have recognized, among other things, that a problem to be solved can include improving access to the nasal and sinus anatomy. The present subject matter can help provide a solution to this problem, such as by compressing or reducing the size of a turbinate.

In some embodiments, the present invention is directed towards a surgical forceps for use in the nasal anatomy of a human. The surgical forceps can include a proximal portion and a distal portion. The proximal portion can include a first handle portion and a second handle portion, where the first handle portion and the second handle portion are configured to be grasped by a hand of a practitioner. The distal portion can be sized or configured to pass through a human nostril and into a nasal passageway, wherein the distal portion includes a jaw portion having a first paddle and a second paddle. The first paddle and the second paddle can be configured to actuate between a fully closed position and an open position when the practitioner moves the first handle portion relative to the second handle portion, wherein the first paddle defines a first flat inner clamping face and the second paddle defines a second flat inner clamping face. A proximal portion of the first flat inner clamping face may not contact the second paddle when the first paddle and the second paddle are in the fully closed position.

The present invention, in some embodiments, also includes methods of compressing a nasal turbinate. The methods may include grasping a surgical forceps with a hand of a practitioner (e.g., a surgical forceps of the present invention) and directing a distal portion of the surgical forceps through a human nostril and into a nasal passageway, wherein the distal portion includes a jaw portion having a first paddle and a second paddle, and wherein the first paddle and the second paddle are configured to actuate between a fully closed position and an open position when the practitioner moves the first handle portion relative to the second handle portion, and wherein the first paddle defines a first flat inner clamping face and the second paddle defines a second flat inner clamping face. The method may further include positioning the jaw portion proximate the nasal turbinate, wherein the first flat inner clamping face is positioned one a first side of the nasal turbinate and the second flat inner clamping face is positioned on a second side of the nasal turbinate opposite the first side. The method may further include compressing the nasal turbinate with the surgical forceps by pressing the first flat inner clamping face against the first side of the nasal turbinate while simultaneously pressing the second flat inner clamping face against the second side of the nasal turbinate.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
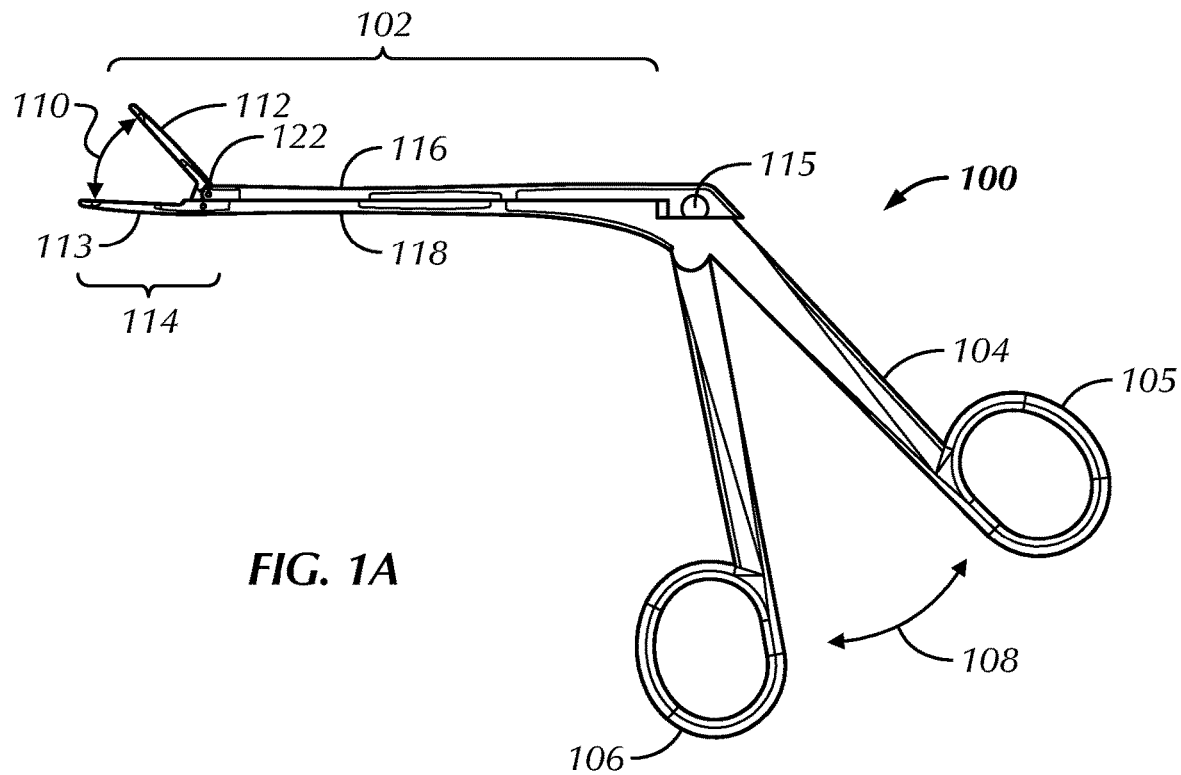
FIGS. 1A and 1B illustrate side views of one embodiment of a surgical forceps of the invention.
Figure 1B:
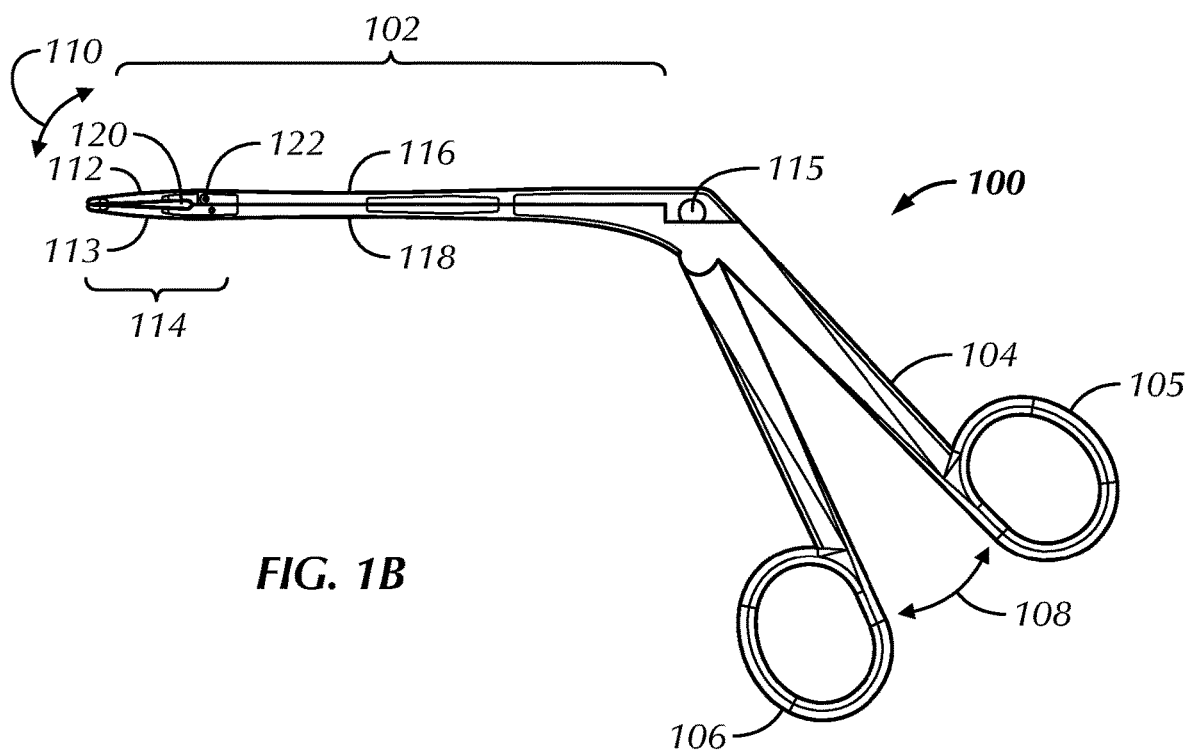
Figure 1C:
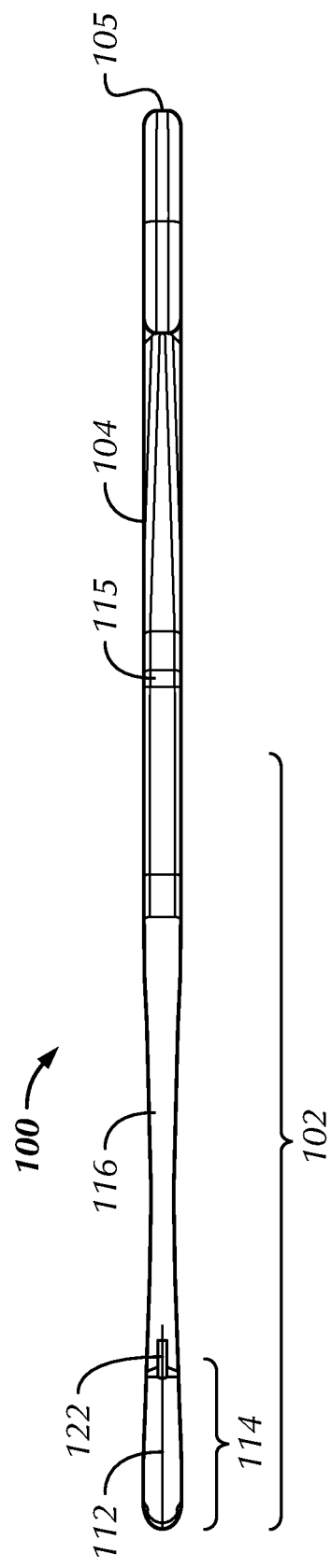
FIG. 1C illustrates a top-down view of the forceps shown in FIGS. 1A and 1B.

FIGS. 1A and 1B illustrate side views of one embodiment of the invention in the form of surgical forceps 100, while FIG. 1C illustrates a top-down view of the same forceps. Surgical forceps 100 include distal portion 102 and proximal portion 104.

Proximal portion 104 includes two handle portions 105 and 106, which are each configured to accommodate a finger of a user or practitioner of the invention. Forceps 100 also includes hinge member 115, about which pivots handle portion 106.

Distal portion 102, which includes a superior arm 116 and an inferior arm 118, may be about 5.5 to about 6 inches in length. The distal end of the inferior arm 118 is attached to or forms inferior paddle 113 while superior arm 116 is attached to superior paddle 112 via hinge member 122. Together, paddles 112 and 113 form a distal jaw portion 114.

One of the main differences between surgical forceps 100 of the present invention and prior art forceps commonly used to treat diseases of the nasal anatomy is that distal jaw portion 114 is configured to apply compressive pressure to a nasal turbinate without removing or significantly cutting the mucosa, bone, or other tissues making up the turbinate structure. That pressure compresses the turbinate into a smaller size to make additional room in the nasal anatomy for performing other surgical procedures, such as a sinus dilation procedures (e.g., a sinus dilation procedure using an inflatable balloon catheter). Depending upon the patient anatomy and the specifics of the surgical procedure, the compressed turbinate tissue should spring back to some extent or even to its original size over the course of minutes, hours, or days.

The portions of surgical forceps 100 that are proximal to jaw portion 114 are similar to comparable proximal portions of prior art surgical forceps commonly used to treat diseases of the nasal anatomy, such as the Blakesley nasal forceps (available from a wide range of surgical instruments suppliers, including from JEDMED of St. Louis, Mo. as their catalog number 54-2992). A user may open and close jaw portion 114 by pivoting handle portion 106 about hinge member 115 and directing the proximal ends of handle portions 105 and 106 away or towards one another along direction 108. In response, superior paddle 112 pivots about hinge member 122, thereby opening and closing paddles 112 and 113 of jaw portion 114 along direction 110. FIG. 1A illustrates forceps 100 when handle portions 105 and 106 are directed fully away from one another, thereby completely opening paddles 112 and 113, while FIG. 1B illustrates forceps 100 when handle portions 105 and 106 are fully directed towards one another, thereby completely closing paddles 112 and 113.

When fully closed, the distal edge of paddle 112 contacts the distal edge of paddle 113 while a triangular space or slight gap 120 is defined between the more proximal portions of the opposing flat faces of paddles 112 and 113, with the "base" of the triangular space (i.e., the widest portion of the gap 120) between the proximal edges of the opposing faces of paddle 112 and the "tip" (i.e., the narrowest portion of the gap 120) at the distal contacting edges of the opposing flat faces of paddles 112 and 113. This slight gap 120 provides for more atraumatic contact between the faces of the paddles 112 and 113 when forceps 100 are compressing a nasal turbinate. As the jaw portion 114 squeezes down on a turbinate, the gap 120 between the proximal surface areas of closed paddles 112 and 113 prevents those more proximal surfaces from excessively compressing the turbinate. In some embodiments, the gap 120 between closed paddles 112 and 113 is widest at the proximal opposing edges of paddles 112 and 113 (i.e., at the proximal portion of jaw portion 114). The gap 120 between the proximal opposing edges of paddles 112 and 113 may be between ~0.5 millimeters and ~5.0 millimeters, between ~0.5 millimeters and ~3 millimeters, between ~0.5 millimeters and 2.0 millimeters, between ~1.0 millimeters and ~2.0 millimeters. In some further embodiments, the gap 120 between the proximal opposing edges of paddles 112 and 113 is approximately 1.5 millimeters.

In some embodiments, when jaw portion 114 is in a closed position, the only points of contact between the superior paddle 112 and inferior paddle 113 at any position distal to hinge member 122 is a line of contact points where the very distal edge of paddles 112 and 113 contact one another along a line. To state it another way, in these embodiments, the opposing faces of paddle 112 and 113 only contact one another along a 1-dimensional straight or curved line rather than over a broader 2-dimensional surface area.

Figure 1D:
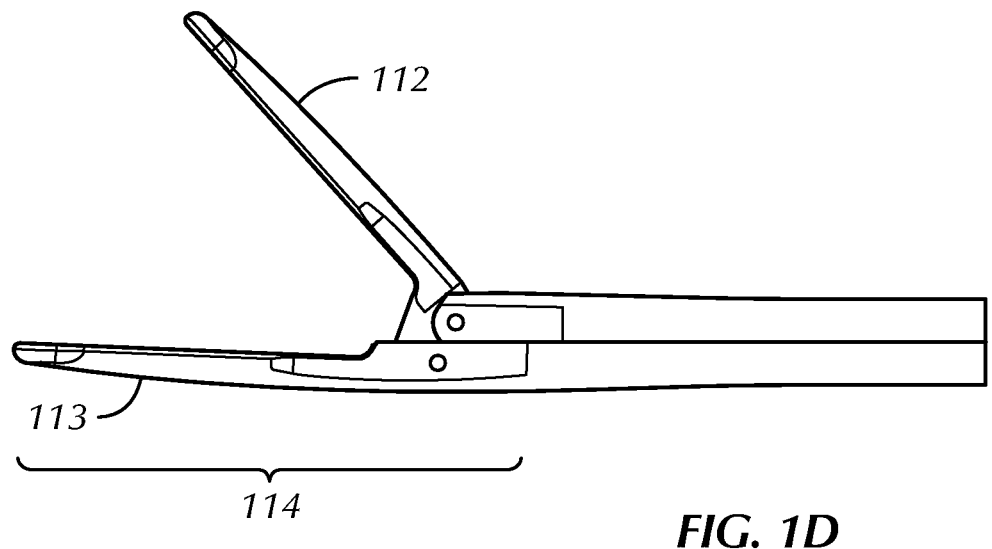
FIG. 1D illustrates a close-up side view of a jaw portion of the forceps shown in FIGS. 1A-1C.

FIG. 1D illustrates a close-up side view of jaw portion 114 when paddles 112 and 113 are in a fully opened position. When fully opened, paddles 112 and 113 may be positioned at an angle of between 35 and 55 degrees.

Figure 2A:
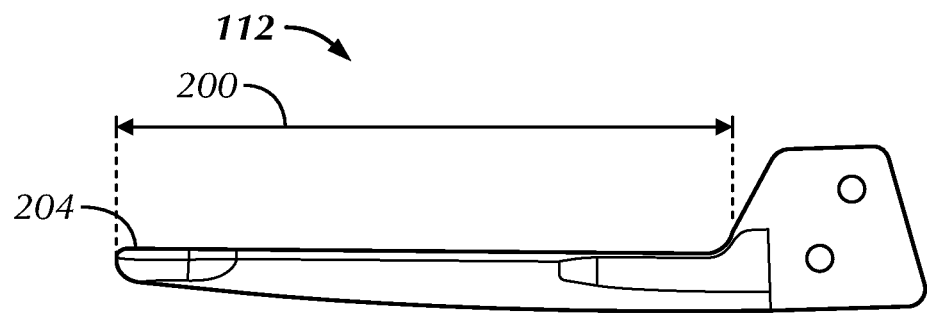
FIGS. 2A-2D illustrate various views of a paddle portion of a forceps of the present invention.
Figure 2B:
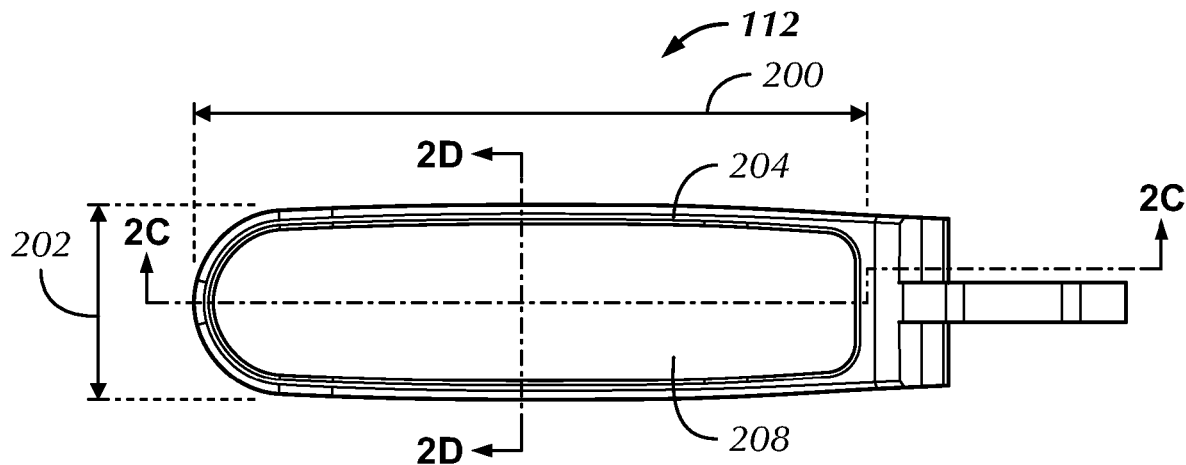
Figure 2C:
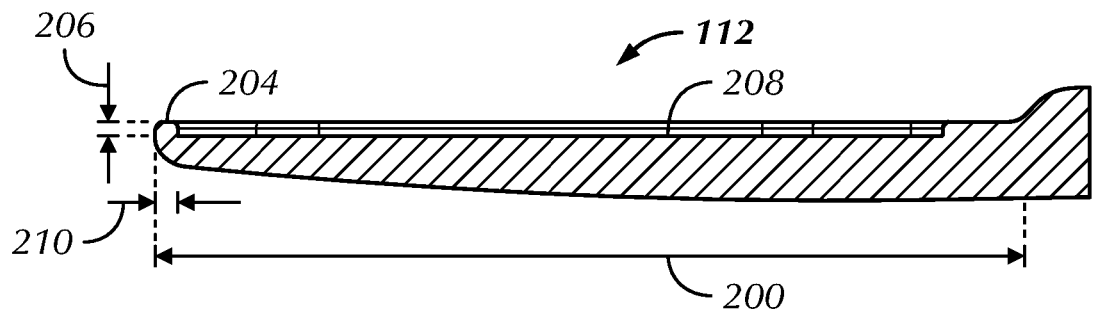
Figure 2D:
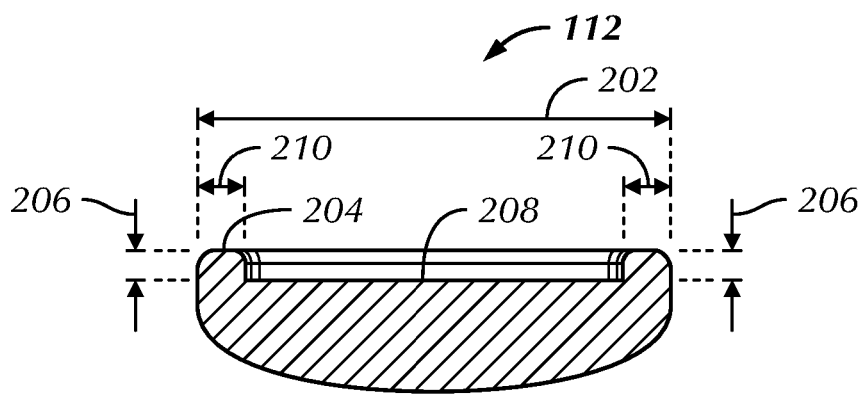

FIGS. 2A-2D illustrate various views of superior paddle 112. FIG. 2A illustrates a close-up side view of a disassembled superior paddle 112, while FIG. 2B illustrates a top view of disassembled superior paddle 112. FIG. 2C illustrates a cut-away view of superior paddle 112 along lines 2C-2C in FIG. 2B, while FIG. 2D illustrates a cut-away view of superior paddle 112 along lines 2D-2D in FIG. 2B.

Paddle 112 has a length 200 of between about 10 and 27 millimeters and a width 202 of between 2 and 10 millimeters. Paddle 112 also has a raised lip 204 that extends around the outer periphery of the flat inner clamping face 208 of paddle 112. With the exception of raised lip 204, inner clamping face 208 defines a flat continuous surface stretching from the raised lip 204 on one side of paddle 112 to the raised lip 204 on the other side of paddle 112 (best illustrated in FIGS. 2C and 2D). Lip 204 rises above or extends from inner clamping face 208 with a height 206 of between 0.005 and 0.025 inches. In some embodiments, height 206 is about 0.15 inches. Lip 204 has a width 210 of between about 0.01 to about 0.03 inches. In some embodiments, width 210 is about 0.02 inches. During use, lip 204 provides surgical forceps 100 with improved gripping of a turbinate while flat inner clamping face 208 provides an atraumatic surface to apply a squeezing pressure to the turbinate without excessive damage to the tissue.

It will be understood that while FIGS. 2A-2D illustrate superior paddle 112, inferior paddle 113 will have a similar, complementary, and symmetrical design. In some embodiments, one of the few differences between superior paddle 112 and inferior paddle 113 is that inferior paddle 113 is formed as a single unitary portion of a distal end of inferior arm 118 and therefore does not include a hinge member that allows inferior paddle 113 to pivot about a point as superior paddle 112 pivots about hinge member 122.

Figure 3A:
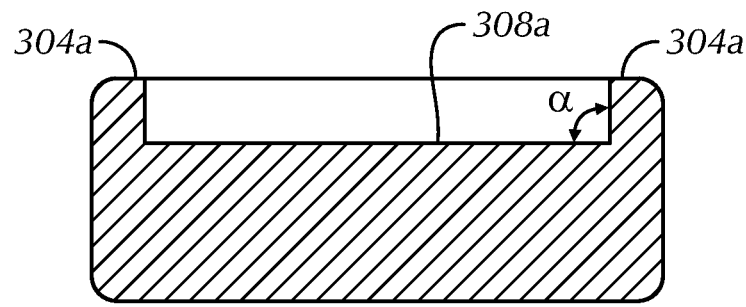
FIGS. 3A-3C illustrate cut-away views of paddle portions of forceps of the present invention.
Figure 3B:
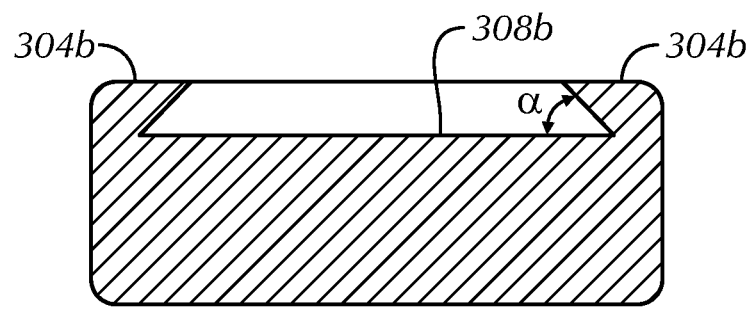
Figure 3C:
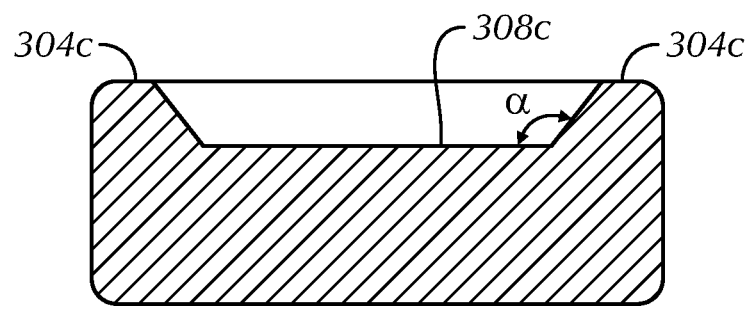

FIGS. 3A-3C illustrate cut-away views of other embodiments of paddles where the raised lips are orientated at different angles relative to the respective inner clamping faces of the paddle. FIG. 3A, for example, illustrates lip 304a which is at a right angle α relative to inner face 308a (similar to the orientation of lip 204 in the embodiments illustrated in FIGS. 2A-2D). FIG. 3B illustrates another embodiment where lip 304b is at an angle α that is acute relative to inner face 308b. FIG. 3C illustrates yet another embodiment, where lip 304c is at an angle α that is obtuse relative to inner face 308c.

Figure 4A:
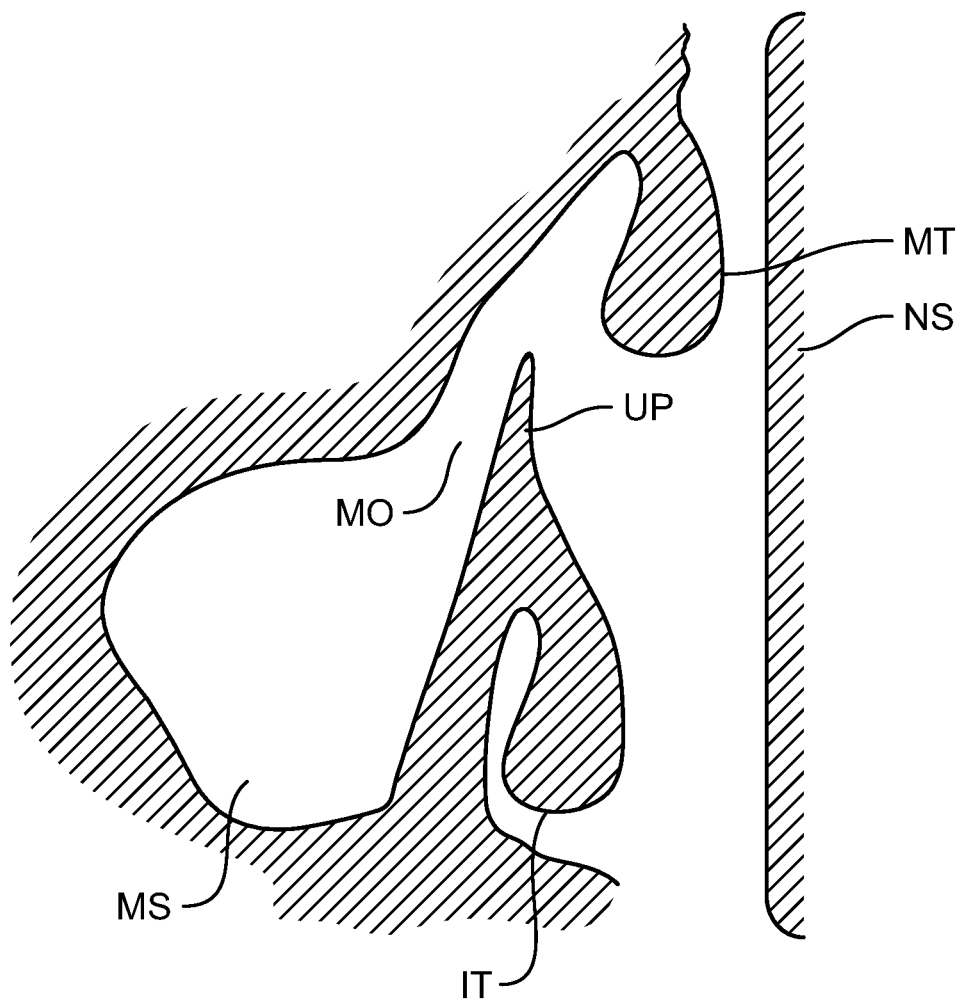
FIGS. 4A-4F illustrate a method of the invention.
Figure 4B:
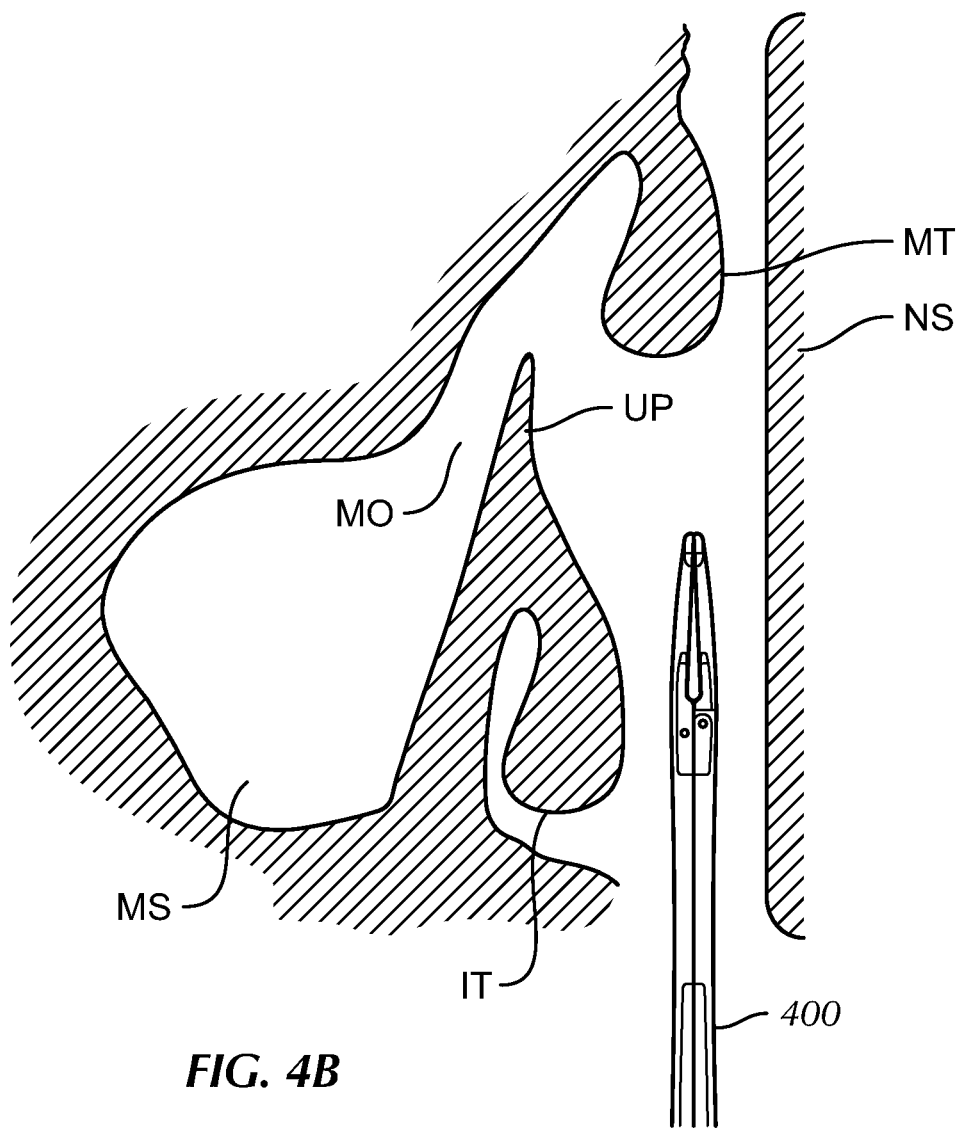

FIGS. 4A-4F illustrate a method of the invention. FIG. 4A shows a diagram of a portion of the human nasal anatomy that includes the maxillary sinus (MS), maxillary ostium (MO), the uncinated process (UT), the inferior and middle turbinates (IT and MT, respectively), and the nasal septum (NS). FIG. 4B illustrates a distal portion of surgical forceps 400 of the present invention entering the nasal anatomy.

Figure 4C:
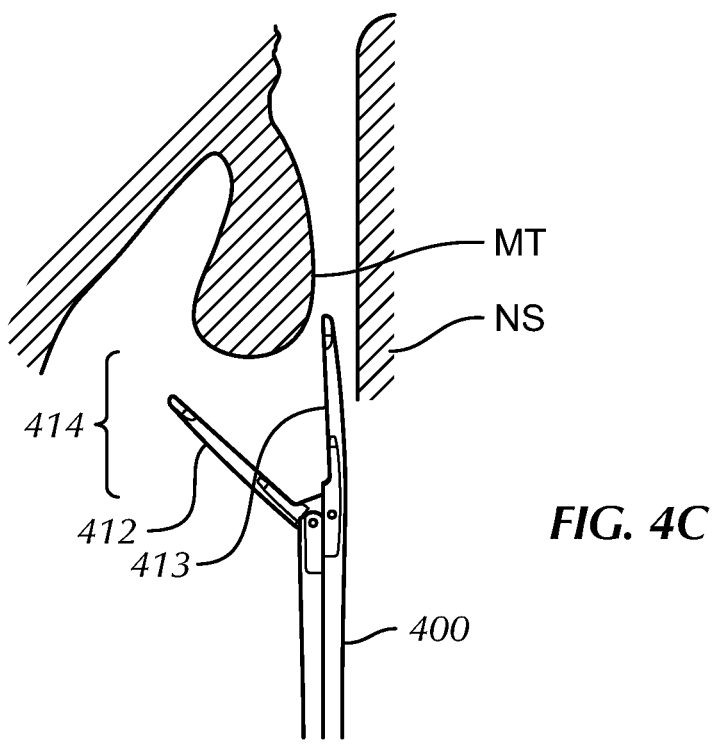

FIG. 4C illustrates a close-up view of jaw portion 414 as it approaches middle turbinate MT. Paddles 412 and 413 of jaw portion 414 are opened by moving handle portions (not illustrated) apart. The jaw portion 414 is advanced further into the anatomy until paddles 412 and 413 are on either side of middle turbinate MT. The operator squeezes middle turbinate MT with the jaw portion 414 by squeezing the handle portions together. While squeezing the middle turbinate MT, the lip and inner faces of the jaw portion 414 engage and press against the tissue of the middle turbinate MT.

Figure 4D:
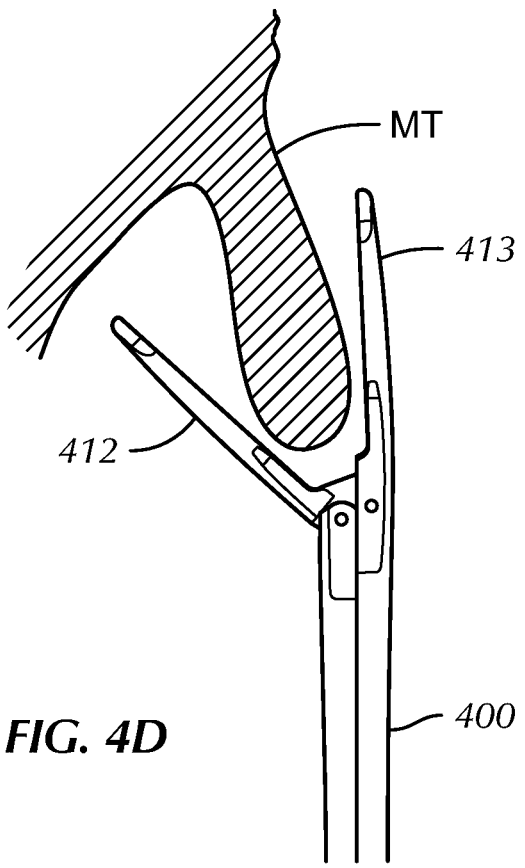
Figure 4E:
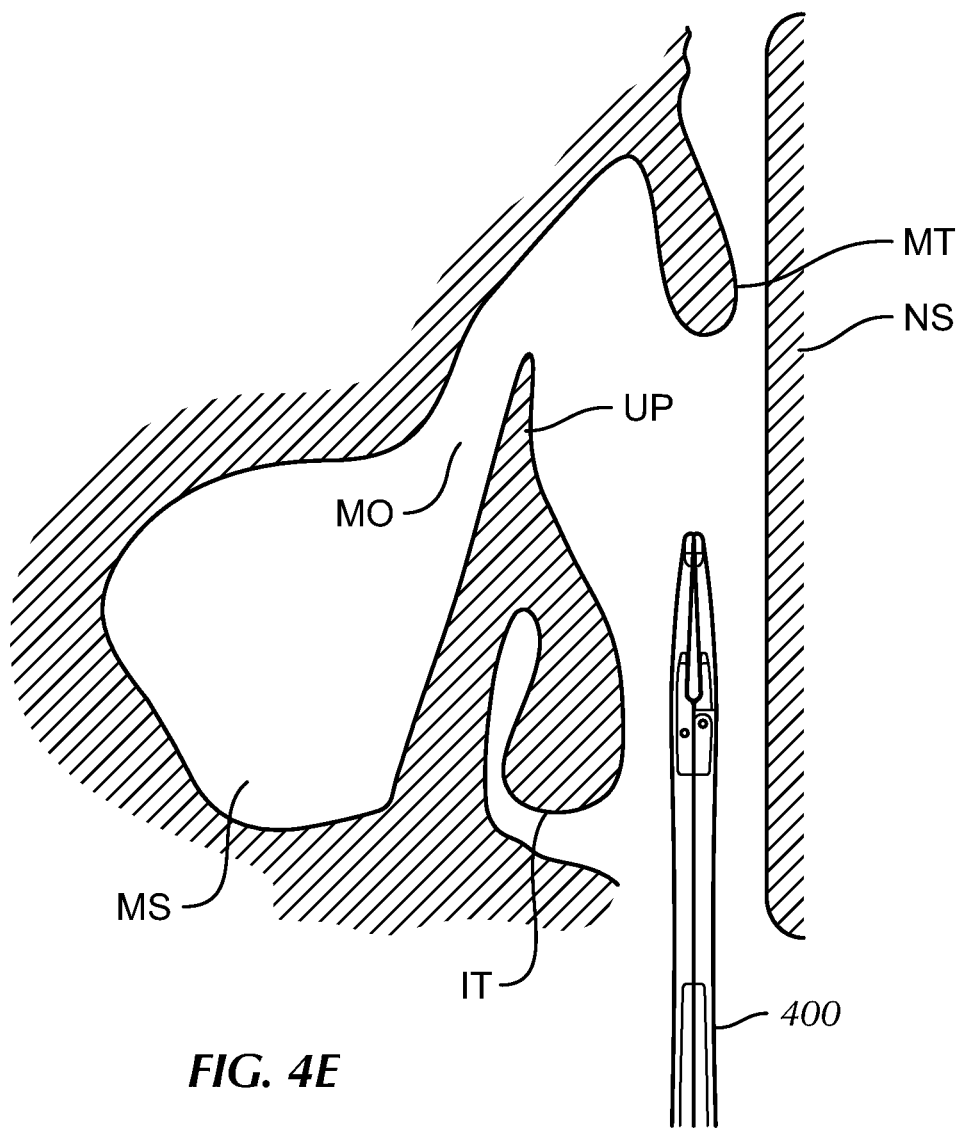
Figure 4F:
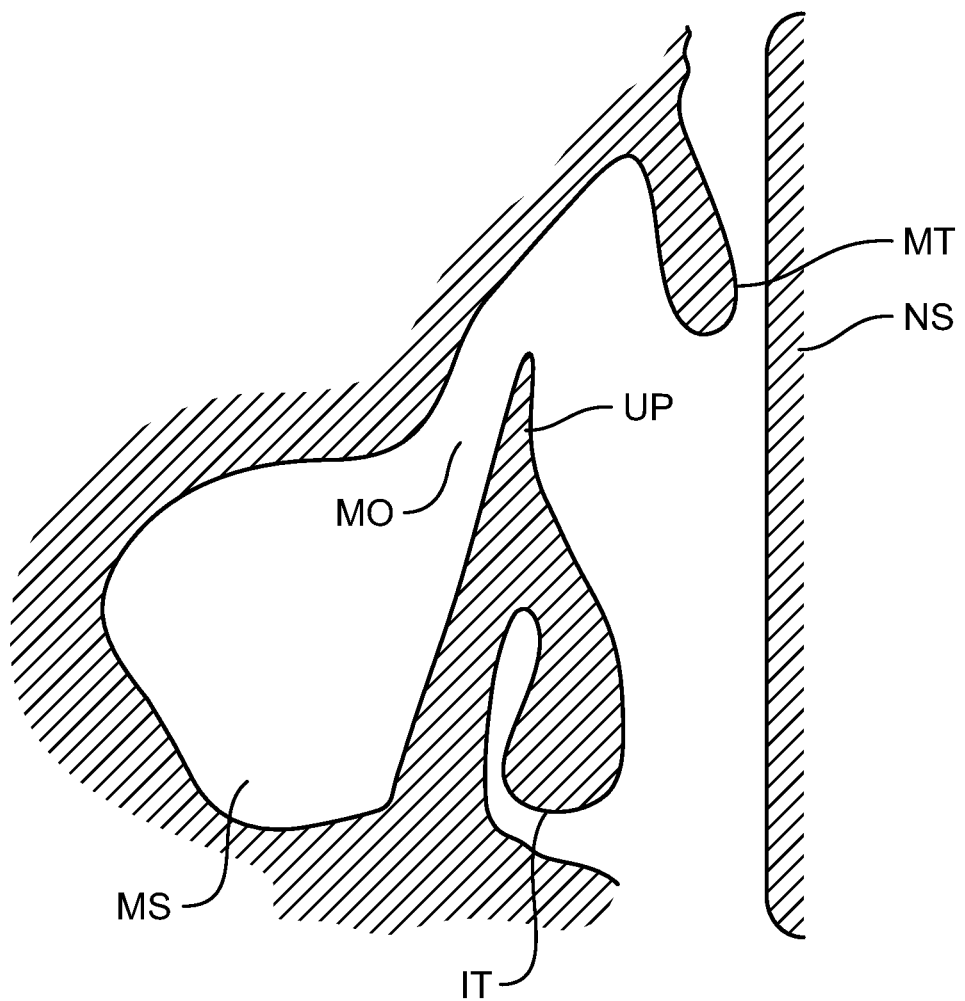

FIG. 4D illustrates a close up view of middle turbinate MT just after surgical forceps 400 has been used to apply pressure to the middle turbinate MT tissue. FIG. 4E illustrates surgical forceps 400 being withdrawn from the nasal anatomy after the middle turbinate MT has been compressed. FIG. 4F illustrates the anatomy just after surgical forceps 400 has been removed, with middle turbinate MT noticeably smaller than prior to the procedure (as shown in FIG. 4A). With the smaller middle turbinate, a health practitioner now has more room to maneuver other instruments (e.g., a sinus dilation balloon). It is believed that the middle turbinate MT will remain in the small configuration for some relatively short period of time (e.g., minutes, hours, or days) and will eventually rebound to some larger size.

ENUMERATED EMBODIMENTS

The following enumerated embodiments are just some examples of the present invention and are not meant to be an exclusive list of all embodiments:

Embodiment 1

A surgical forceps for use in the nasal anatomy of a human, the surgical forceps comprising:
- a proximal portion that includes a first handle portion and a second handle portion, the first handle portion and the second handle portion configured to be grasped by a hand of a practitioner;
- a distal portion configured to pass through a human nostril and into a nasal passageway, wherein the distal portion includes a jaw portion having a first paddle and a second paddle;
- wherein the first paddle and the second paddle are configured to actuate between a fully closed position and an open position when the practitioner moves the first handle portion relative to the second handle portion, and wherein the first paddle defines a first flat inner clamping face and the second paddle defines a second flat inner clamping face, and wherein a proximal portion of the first flat inner clamping face does not contact the second paddle when the first paddle and the second paddle are in the fully closed position.

Embodiment 2

The surgical forceps of Embodiment 1, wherein a distal portion of the first flat inner clamping face contacts the second paddle when the first paddle and the second paddle are in the fully closed position.

Embodiment 3

The surgical forceps of either Embodiments 1 or 2, wherein the first paddle has a length of between 10 and 27 millimeters and a width of between 2 and 10 millimeters.

Embodiment 4

The surgical forceps of any of Embodiments 1-3, wherein the first paddle includes a raised lip, wherein the raised lip extends from the first flat inner clamping face and extends about a periphery of the first flat inner clamping face.

Embodiment 5

The surgical forceps of any of Embodiments 1-4, wherein the raised lip has a height of between 0.005 and 0.025 inches and a width of between 0.01 and 0.03 inches.

Embodiment 6

The surgical forceps of any of Embodiments 1-5, wherein the raised lip is orientated at a right angle relative to the first flat inner clamping face.

Embodiment 7

The surgical forceps of any of Embodiment 1-5, wherein the raised lip is orientated at an acute angle relative to the first flat inner clamping face.

Embodiment 8

The surgical forceps of any of Embodiment 1-5, wherein the raised lip is orientated at an obtuse angle relative to the first flat inner clamping face.

Embodiment 9

A method of compressing a nasal turbinate, the method including:
- grasping a surgical forceps (e.g., any of the forceps described in any of Embodiments 1-8), wherein the surgical forceps include a first handle portion and a second handle portion that are both grasped by a hand of a practitioner;
- directing a distal portion of the surgical forceps through a human nostril and into a nasal passageway, wherein the distal portion includes a jaw portion having a first paddle and a second paddle, and wherein the first paddle and the second paddle are configured to actuate between a fully closed position and an open position when the practitioner moves the first handle portion relative to the second handle portion, and wherein the first paddle defines a first flat inner clamping face and the second paddle defines a second flat inner clamping face;
- positioning the jaw portion proximate the nasal turbinate, wherein the first flat inner clamping face is positioned one a first side of the nasal turbinate and the second flat inner clamping face is positioned on a second side of the nasal turbinate opposite the first side; and
- compressing the nasal turbinate with the surgical forceps by pressing the first flat inner clamping face against the first side of the nasal turbinate while simultaneously pressing the second flat inner clamping face against the second side of the nasal turbinate.

Embodiment 10

The method of Embodiment 9, wherein the surgical forceps are configured so that a proximal portion of the first flat inner clamping face does not contact the second paddle when the first paddle and the second paddle are in the fully closed position Embodiment 11

The method of either Embodiments 9 or 10, wherein the surgical forceps are configured so that a distal portion of the first flat inner clamping face contacts the second paddle when the first paddle and the second paddle are in the fully closed position.

Embodiment 12

The method of any of Embodiments 9-11, wherein the first paddle has a length of between 10 and 27 millimeters and a width of between 2 and 10 millimeters.

Embodiment 13

The method of any of Embodiments 9-12, wherein the first paddle includes a raised lip, wherein the raised lip extends from the first flat inner clamping face and extends about a periphery of the first flat inner clamping face.

Embodiment 14

The method of any of Embodiments 9-13, wherein the raised lip has a height of between 0.005 and 0.025 inches and a width of between 0.01 and 0.03 inches.

Embodiment 15

The method of any of Embodiments 9-14, wherein the raised lip is orientated at a right angle relative to the first flat inner clamping face.

Embodiment 16

The method of any of Embodiments 9-14, wherein the raised lip is orientated at an acute angle relative to the first flat inner clamping face.

Embodiment 17

The method of any of Embodiments 9-14, wherein the raised lip is orientated at an obtuse angle relative to the first flat inner clamping face.

Embodiment 18

The method of any of Embodiments 9-17, wherein compressing the nasal turbinate does not include using the surgical forceps to remove tissue from the nasal turbinate.

Embodiment 19

The method of any of Embodiments 9-18, further including performing a surgical procedure in the nasal anatomy after compressing the nasal turbinate.

Embodiment 20

The method of any of Embodiment 19, wherein the surgical procedure is a sinus dilation procedure.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Any numerical ranges recited above shall be read as including support for any sub-ranges as if said sub-ranges were explicitly recited herein. For example, if a range of 1-10 is described, then it shall be understood that the range supports any subrange between 1 and 10, such as 1-3, 3-7, or 3.6 to 9.874.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of compressing a nasal turbinate, the method including:

grasping a surgical forceps, wherein the surgical forceps include a first handle portion and a second handle portion that are both grasped by a hand of a practitioner;

directing a distal portion of the surgical forceps through a human nostril and into a nasal passageway, wherein the distal portion includes a jaw portion having a first paddle and a second paddle, and wherein the first paddle and the second paddle are configured to actuate between a fully closed position and an open position when the practitioner moves the first handle portion relative to the second handle portion, and wherein the first paddle defines a first flat inner clamping face and the second paddle defines a second flat inner clamping face;

positioning the jaw portion proximate a nasal turbinate, wherein the first flat inner clamping face is positioned on a first side of the nasal turbinate and the second flat inner clamping face is positioned on a second side of the nasal turbinate opposite the first side; and compressing the nasal turbinate with the surgical forceps by pressing the first flat inner clamping face against the first side of the nasal turbinate while simultaneously pressing the second flat inner clamping face against the second side of the nasal turbinate.

2. The method of claim 1, wherein the surgical forceps are configured so that a proximal portion of the first flat inner clamping face does not contact the second paddle when the first paddle and the second paddle are in the fully closed position.

3. The method of claim 1, wherein the surgical forceps are configured so that a distal portion of the first flat inner clamping face contacts the second paddle when the first paddle and the second paddle are in the fully closed position.

4. The method of claim 1, wherein the first paddle has a length of between 10 millimeters and 27 millimeters and a width of between 2 millimeters and 10 millimeters.

5. The method of claim 1, wherein the first paddle includes a raised lip, wherein the raised lip extends from the first flat inner clamping face and extends about a periphery of the first flat inner clamping face.

6. The method of claim 5, wherein the raised lip has a height of between 0.005 inches and 0.025 inches and a width of between 0.01 inches and 0.03 inches.

7. The method of claim 5, wherein the raised lip is orientated at a right angle relative to the first flat inner clamping face.

8. The method of claim 5, wherein the raised lip is orientated at an acute angle relative to the first flat inner clamping face.

9. The method of claim 5, wherein the raised lip is orientated at an obtuse angle relative to the first flat inner clamping face.

10. The method of claim 1, wherein compressing the nasal turbinate does not include using the surgical forceps to remove tissue from the nasal turbinate.

11. The method of claim 1, further including performing a surgical procedure in an nasal anatomy after compressing the nasal turbinate.

12. The method of claim 11, wherein the surgical procedure is a sinus dilation procedure.

13. A method of performing a surgical procedure on nasal anatomy, comprising:

directing a distal portion of a surgical forceps through a human nostril and into a nasal passageway, wherein the distal portion comprises a jaw portion having a first paddle and a second paddle, wherein the first paddle defines a first flat inner clamping face and the second paddle defines a second flat inner clamping face;

actuating a first handle portion of the surgical forceps relative to a second handle portion of the surgical forceps to actuate the first paddle and the second paddle from a fully closed position to an open position;

while the first paddle and the second paddle are in the open position, positioning the jaw portion at a position proximate to a nasal turbinate such that the first flat inner clamping face is on a first side of the nasal turbinate and the second flat inner clamping face is on a second side of the nasal turbinate opposite the first side;

after positioning the jaw portion at the position proximate to the nasal turbinate, compressing the nasal turbinate with the surgical forceps by pressing the first flat inner clamping face against the first side of the nasal turbinate while simultaneously pressing the second flat inner clamping face against the second side of the nasal turbinate, wherein the nasal turbinate has a first size prior to compressing the nasal turbinate and a second size after compressing the nasal turbinate, wherein the second size is smaller than the first size;

after compressing the nasal turbinate, withdrawing the distal portion of the surgical forceps from the human nostril, wherein a size of the nasal turbinate remains smaller than the first size for a period of time after withdrawing the distal portion of the surgical forceps from the human nostril; and after withdrawing the distal portion of the surgical forceps, performing a surgical procedure on the nasal anatomy during the period of time in which the size of the nasal turbinate remains smaller than the first size.

14. The method of claim 13, wherein performing the surgical procedure comprises performing a sinus dilation procedure.

15. The method of claim 13, wherein the first paddle comprises a first raised lip that extends around an outer periphery of the first flat inner clamping face, and
wherein the second paddle comprises a second raised lip that extends around an outer periphery of the second flat inner clamping face.

16. The method of claim 13, wherein, in the fully closed position, a gap is defined by a proximal portion of the first paddle and a proximal portion of the second paddle.

17. The method of claim 13, wherein compressing the nasal turbinate comprises compressing the nasal turbinate without removing or cutting any anatomical structure selected from mucosa, bone, and tissue of the nasal turbinate.

18. The method of claim 13, wherein the nasal turbinate is a middle turbinate.

19. The method of claim 13, wherein directing the distal portion of the surgical forceps through the human nostril and into the nasal passageway is performed while the first paddle and the second paddle are in the fully closed position.

20. The method of claim 13, further comprising allowing the nasal turbinate to return to the first size.

* * * * *